US009928618B2

(12) United States Patent
Lee et al.

(10) Patent No.: US 9,928,618 B2
(45) Date of Patent: Mar. 27, 2018

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Jae Hak Lee, Yongin-si (KR); Dong Goo Kang, Hwaseong-si (KR); Young Hun Sung, Hwaseong-si (KR); Jae Mock Yi, Hwaseong-si (KR); Ji Young Choi, Suwon-si (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 238 days.

(21) Appl. No.: 14/517,193

(22) Filed: Oct. 17, 2014

(65) Prior Publication Data

US 2015/0117606 A1 Apr. 30, 2015

(30) Foreign Application Priority Data

Oct. 24, 2013 (KR) ........................ 10-2013-0127174

(51) Int. Cl.
*A61B 6/00* (2006.01)
*G06T 11/00* (2006.01)
*A61B 6/06* (2006.01)
*G06T 7/30* (2017.01)

(52) U.S. Cl.
CPC .............. *G06T 11/005* (2013.01); *A61B 6/06* (2013.01); *A61B 6/487* (2013.01); *A61B 6/5235* (2013.01); *A61B 6/5264* (2013.01); *G06T 7/30* (2017.01); *A61B 6/40* (2013.01); *A61B 6/4441* (2013.01); *A61B 6/4464* (2013.01); *A61B 6/469* (2013.01); *G06T 2207/10116* (2013.01)

(58) Field of Classification Search
CPC ............ A61B 6/03; A61B 6/469; A61B 6/487
See application file for complete search history.

(56) References Cited

U.S. PATENT DOCUMENTS

| 6,501,828 | B1 * | 12/2002 | Popescu | .................... A61B 6/06 378/145 |
| 8,325,801 | B2 | 12/2012 | Lei et al. | |
| 2003/0058994 | A1 * | 3/2003 | Sembritzki | .............. A61B 6/06 378/108 |
| 2010/0124276 | A1 | 5/2010 | Zhou | |
| 2010/0191113 | A1 | 7/2010 | Hazard et al. | |
| 2010/0272238 | A1 | 10/2010 | Machan et al. | |

(Continued)

FOREIGN PATENT DOCUMENTS

KR     10-1200974 B1     11/2012

*Primary Examiner* — Dani Fox
(74) *Attorney, Agent, or Firm* — Sughrue Mion, PLLC

(57) ABSTRACT

An X-ray imaging apparatus is provided. The X-ray imaging apparatus includes an X-ray generator configured to radiate X-rays onto an object having a region of interest (ROI) and a non-ROI, a filter configured to adjust an X-ray dose of the X-rays incident on the ROI and the non-ROI, an X-ray detector configured to detect the X-rays transmitted through the object and convert the X-rays into X-ray data, and an image processing unit configured to obtain a frame image using the X-ray data, register the obtained frame image to a previous frame image, synthesize the frame image and the previous frame image, and generate a reconstructed frame image.

13 Claims, 12 Drawing Sheets

(56) References Cited

U.S. PATENT DOCUMENTS

| | | | |
|---|---|---|---|
| 2012/0215095 A1* | 8/2012 | Av-Shalom | A61B 6/06 600/424 |
| 2014/0198131 A1* | 7/2014 | Rudin | A61B 6/12 345/634 |
| 2015/0078516 A1* | 3/2015 | Ohashi | A61B 6/06 378/42 |

* cited by examiner

X-RAY IMAGING APPARATUS AND METHOD OF CONTROLLING THE SAME

CROSS-REFERENCE TO RELATED APPLICATION

This application claims priority from Korean Patent Application No. 10-2013-0127174, filed on Oct. 24, 2013 in the Korean Intellectual Property Office, the disclosure of which is incorporated herein by reference in its entirety.

BACKGROUND

1. Technical Field

Apparatuses and methods consistent with exemplary embodiments relate to an X-ray imaging apparatus and a method of controlling the same, and more specifically, to an X-ray imaging apparatus that reconstructs a current frame using previous frame information and a method of controlling the same.

2. Description of the Related Art

An X-ray imaging apparatus is an apparatus capable of obtaining an internal image of an object by radiating X-rays onto the object and collecting the X-rays transmitted through the object. Because the permeability of objects, materials, and/or elements within the object differ with regards to allowing X-rays to pass through depending on properties of substances composing the object, it is possible to image an internal structure of the object by detecting an intensity or a strength of X-rays transmitted through the object.

In order to provide a level of safety from the X-ray imaging apparatus, reducing a dose of X-rays incident on the object is recognized as an important issue and thus a great deal of research and development for reducing an X-ray dose is underway. One technological implementation for reducing an X-ray dose includes a method of radiating X-rays onto only a region of interest which has been generally adopted.

SUMMARY

According to an aspect of an exemplary embodiment, there is provided an X-ray imaging apparatus including an X-ray generator configured to radiate X-rays onto an object having a region of interest (ROI) and a non-ROI, a filter configured to adjust an X-ray dose of the X-rays incident on the ROI and the non-ROI, an X-ray detector configured to detect the X-rays transmitted through the object and convert the X-rays into X-ray data, and an image processing unit configured to obtain a frame image using the X-ray data, register the obtained frame image to a previous frame image, synthesize the frame image and the previous frame image, and generate a reconstructed frame image.

The filter may include a filter sheet including an open area corresponding to the ROI and a closed area corresponding to the non-ROI, and a driver configured to move the open area of the filter sheet.

The X-ray imaging apparatus may further include a controller configured to provide a control signal to the driver for moving the open area of the filter sheet.

When the ROI of the object moves, the controller may generate the control signal based on movement information of the ROI, provide the generated control signal to the driver, and the driver may use the generated control signal to move the filter sheet such that the open area of the filter sheet corresponds to the moving ROI.

The image processing unit may include an image analyzer configured to analyze X-ray data and obtain the frame image in which the ROI and the non-ROI are set, an image registration unit configured to register the obtained frame image to the previous frame image, and an image synthesizing unit configured to synthesize the frame image and the registered previous frame image.

The image processing unit may further include an image adjuster configured to adjust brightness and contrast of the non-ROI to have a predetermined value.

The image adjuster may remove noise from the non-ROI.

According to an aspect of another exemplary embodiment, there is provided a method of controlling an X-ray imaging apparatus, including radiating X-rays onto an object having a region of interest (ROI) and a non-ROI, detecting X-rays transmitted through the object, obtaining a frame image of the object using the detected X-rays, registering the obtained frame image to a previous frame image, and generating a reconstructed frame image by synthesizing the frame image and the registered previous frame image.

The radiating of the X-rays onto the object may further include filtering the radiating X-rays such that an X-ray dose on the non-ROI is smaller than on the non-ROI of the object.

The method may further include setting the ROI and the non-ROI in the obtained frame image after the obtaining of the frame image.

The method may further include performing image processing on the non-ROI of the frame image after the setting of the ROI and the non-ROI.

The performing of the image processing may include adjusting brightness and contrast of the non-ROI of the frame image to have a predetermined value.

The performing of the image processing may further include removing noise from the non-ROI of the frame image.

The method may further include performing image processing on the non-ROI of the generated reconstructed frame image after the generating of the reconstructed frame image.

The performing of the image processing may include adjusting brightness and contrast of the non-ROI of the reconstructed frame image to have a predetermined value.

The performing of the image processing may further include removing noise from the non-ROI of the reconstructed frame image.

BRIEF DESCRIPTION OF THE DRAWINGS

The above and/or other aspects will become apparent and more readily appreciated from the following description of exemplary embodiments, taken in conjunction with the accompanying drawings, in which.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, exemplary embodiments will now be described more fully hereinafter with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. The scope is defined not by the detailed description but by the appended claims. Like numerals denote like elements throughout.

Hereinafter, exemplary embodiments will be described in detail with reference to the accompanying drawings.

An X-ray imaging apparatus may have a different structure or imaging method depending on a region to be imaged, a type of an X-ray image, or a purpose of imaging. Specifically, there are a general X-ray imaging apparatus for imaging a chest, arms, legs, or the like, an X-ray imaging apparatus using mammography as mammography technology, an X-ray imaging apparatus using fluoroscopy, an X-ray imaging apparatus using angiography, an X-ray imaging apparatus for cardiography, and an X-ray imaging apparatus using tomography. An X-ray imaging apparatus according to an exemplary embodiment may be one of the above-described X-ray imaging apparatuses or a combination thereof.

Figure 1:
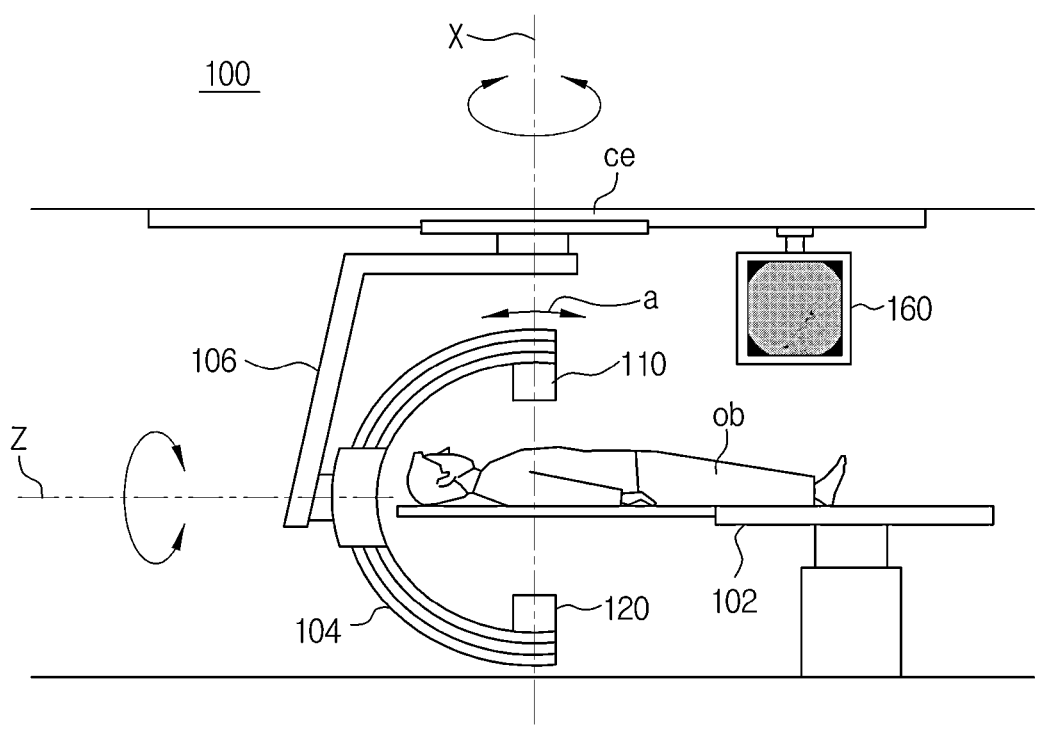
FIG. 1 is a diagram illustrating an appearance of an X-ray imaging apparatus according to an exemplary embodiment.

FIG. 1 is a diagram illustrating an appearance of an X-ray imaging apparatus according to an exemplary embodiment.

As illustrated in FIG. 1, an X-ray imaging apparatus 100 may include an X-ray generator 110 and an X-ray detector 120 facing the X-ray generator 110.

The X-ray generator 110 may generate X-rays in order to obtain an X-ray image of an object (ob) and radiate the generated X-rays onto the object (ob).

The X-ray detector 120 may detect X-rays transmitted through the object (ob). In addition, the X-ray detector 120 may convert the detected X-rays into X-ray data, which is an electrical signal.

Here, the object (ob) may be a body of human or animal, but the object is not limited thereto. The object (ob) may include any object of which an internal structure can be imaged by the X-ray imaging apparatus 100.

The X-ray imaging apparatus 100 may further include a table 102 that accommodates the object (ob). Accordingly, while the X-ray generator 110 radiates X-rays, the object (ob) is accommodated on the table 102 and is positioned between the X-ray generator 110 and the X-ray detector 120.

As illustrated in FIG. 1, the X-ray generator 110 and the X-ray detector 120 may be provided in both facing ends of a C-arm 104. The C-arm 104 is rotatably mounted around a horizontal axis indicated by a Z-axis. In addition, the C-arm 104 may rotate in a circular or semicircular shape in an arrow direction (a). The C-arm 104 may be mounted on a supporting unit 106 installed in a ceiling (ce). The supporting unit 106 may rotate around a vertical axis indicated by an X-axis. Therefore, when the C-arm 104 and the supporting unit 106 are rotated, X-ray images of various regions of interest (ROIs) of the object (ob) may be obtained in various directions.

An X-ray image of the object (ob) obtained by performing predetermined image processing on an electrical signal of X-rays detected by the X-ray detector 120 may be displayed on a display 160. In this case, although the display 160 is installed in the ceiling (ce) in FIG. 1, a position of the display 160 is not limited thereto.

Figure 2:
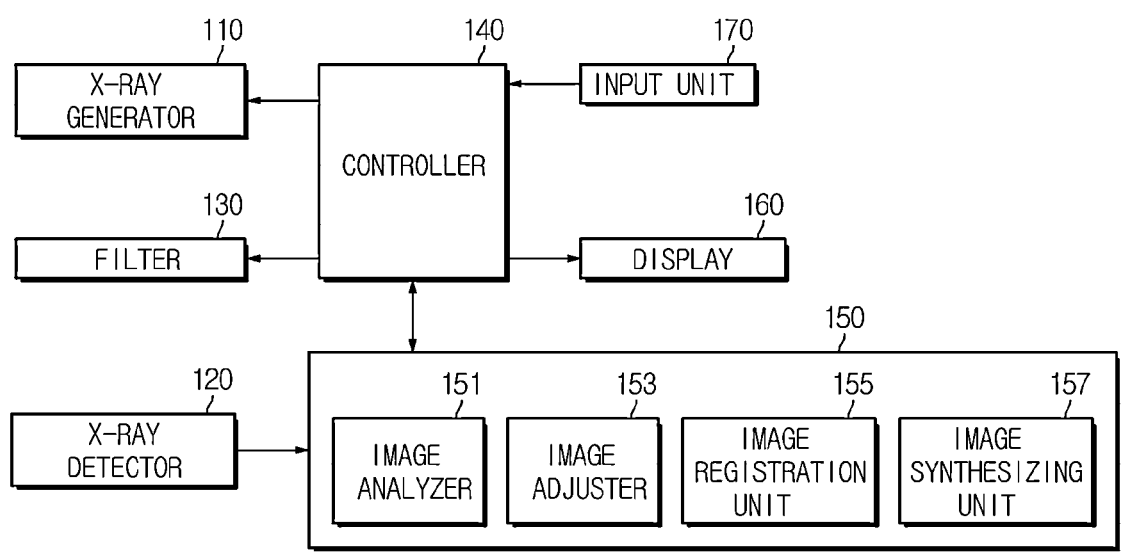
FIG. 2 is a block diagram illustrating a configuration of an X-ray imaging apparatus according to an exemplary embodiment.

According to another exemplary embodiment, the X-ray imaging apparatus 100 may further include an input unit 170 (refer to FIG. 2). Examples of the input unit 170 may include a switch, a keyboard, a trackball, and a touch screen, but one or more exemplary embodiments are not limited thereto.

Examples of the display 160 may include a cathode ray tube (CRT), a liquid crystal display (LCD), a light emitting diode (LED) display, and an organic light emitting diode (OLED) display, but one or more exemplary embodiments are not limited thereto.

The appearance of the X-ray imaging apparatus has been described. Hereinafter, an internal configuration of the X-ray imaging apparatus according to the exemplary embodiment will be described in detail.

FIG. 2 is a block diagram illustrating a configuration of the X-ray imaging apparatus according to the exemplary embodiment.

As illustrated in FIG. 2, the X-ray imaging apparatus 100 according to the exemplary embodiment may include the X-ray generator 110, the X-ray detector 120, a filter 130, a controller 140, an image processing unit 150, the input unit 170, and the display 160.

The X-ray generator 110 is configured to generate X-rays and radiate the generated X-rays onto the object (ob). The X-ray generator 110 is supplied with power from a power supplying unit and generates X-rays. X-ray energy may be controlled by tube voltage and a strength or a dose of X-rays may be controlled by tube current and an X-ray exposure time.

In the exemplary embodiment, the X-ray generator 110 may radiate single energy X-rays having low energy or high energy, or multi-energy X-rays having low energy X-rays and high energy X-rays.

The X-ray imaging apparatus 100 according to the exemplary embodiment may generate an X-ray video having a plurality of frame images by applying X-ray fluoroscopy. Such an X-ray video may be applied to the field of X-ray diagnosis such as angiography or various operation fields using the same. This X-ray video may be generated and displayed in real time.

In this way, in order to generate the X-ray video having a plurality of frame images, the X-ray imaging apparatus 100 needs to consecutively perform X-ray imaging. In this case, consecutively performing X-ray imaging may be understood as X-rays being consecutively radiated onto the object (ob) and X-rays transmitted through the object (ob) being consecutively detected.

A continuous exposure method and a pulse exposure method may be used as a method of consecutively performing X-ray imaging. In the continuous exposure method, low tube current is continuously supplied to an X-ray tube 111 (refer to FIG. 3) and X-rays are continuously radiated onto the object (ob). In the pulse exposure method, a pulse signal having a constant interval is provided to the X-ray tube 111 and X-rays are multiply radiated onto the object (ob) at a constant interval. Between the two methods, in the pulse exposure method, because X-rays are multiply radiated at a constant interval, it is possible to reduce the X-ray dose incident on the object (ob) and motion blurring.

The X-ray imaging apparatus 100 according to an exemplary embodiment may use both of the two methods. Hereinafter, for convenience of description, description will be made with the pulse exposure method as an example.

The X-ray generator 110 may radiate X-rays onto the object (ob) multiple times according to a predetermined time interval or any time interval input by a user. Here, the predetermined time interval or any time interval may be determined by a pulse rate or a frame rate, and the pulse rate may be determined by the frame rate. For example, the frame rate may be set to, for example, 30 frames per second (30 fps) or 7.5 frames per second (7.5 fps).

The X-ray generator 110 may radiate monochromatic X-rays or polychromatic X-rays. The X-ray generator 110 may include the X-ray tube 111 configured to generate X-rays.

Figure 3:
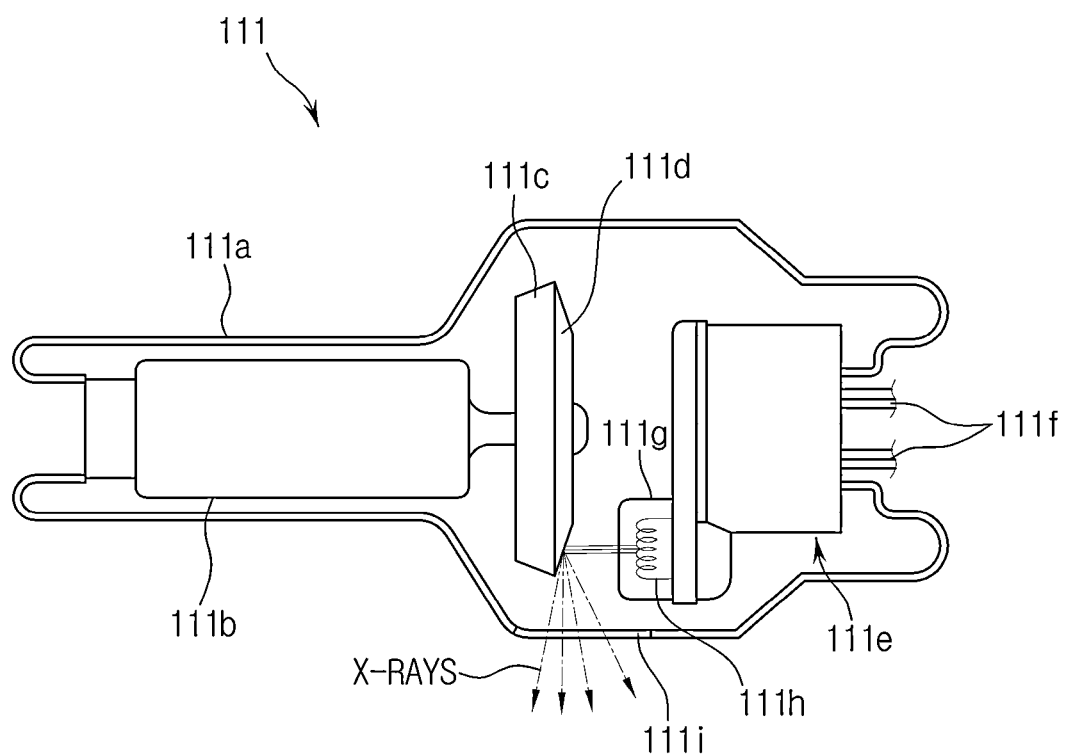
FIG. 3 is a cross-sectional view illustrating an internal structure of an X-ray tube according to an exemplary embodiment.

FIG. 3 is a diagram illustrating a structure of the X-ray tube 111 according to an exemplary embodiment.

As illustrated in FIG. 3, the X-ray tube 111 may be implemented as a diode including an anode 111c and a cathode 111e. A tube body may be a glass tube 111a made of, for example, silica hard glass.

The cathode 111e includes a filament 111h and a focusing electrode 111g configured to focus electrons. The focusing electrode 111g is also referred to as a focusing cup. An inside of the glass tube 111a is maintained in a high vacuum state of about 10 mmHg, the filament 111h of the cathode is heated to a high temperature, and thermoelectrons are generated. In this case, a tungsten (W) filament may be used as the filament 111h, but one or more exemplary embodiments are not limited thereto. The thermoelectrons may be generated by applying current to an electrical conductor 111f connected to the filament 111h. Although the filament 111h is used in the cathode 111e in FIG. 3, this is only an example, and it is also possible to use, for example, a carbon nanotube capable of being driven in a high-speed pulse as the cathode 111e.

The anode 111c, according to an exemplary embodiment, may be mainly made of copper (Cu), and a target material 111d may be formed in a side facing the cathode 111e. Here, a high-resistance material such as chromium (Cr), iron (Fe), cobalt (Co), nickel (Ni), tungsten (W), and molybdenum (Mo) may be used as the target material (C), but one or more exemplary embodiments are not limited thereto. In this case, as a melting point of the target material (C) increases, a focal spot size may decrease.

When high voltage is applied between the cathode 111e and the anode 111c, thermoelectrons generated from the filament 111h are accelerated and collide with the target material 111d of the anode 111c, and thus X-rays are generated. The generated X-rays may be radiated to the outside through a window 111i. In this case, a beryllium (Be) film may be used as the window 111i, but one or more exemplary embodiments are not limited thereto.

The target material 111d may be rotated by a rotor 111b. When the target material 111d is rotated, a heat accumulation rate per unit area may be ten times or more that of a fixed state of the target material 111d and the focal spot size may decrease.

Voltage applied between the cathode 111e and the anode 111c of the X-ray tube 111 is referred to as tube voltage, and a level thereof may be indicated as peak kilovoltage (kVp). As the tube voltage increases, acceleration of thermoelectron emission increases. As a result, energy (photon energy) generated by the X-rays colliding with the target material 111d may increase. In this case, the tube voltage of 70 kVp to 120 kVp may be generally applied, but one or more exemplary embodiments are not limited thereto.

Current flowing in the X-ray tube 111 is referred to as tube current and may be indicated as an average mA. As the tube current increases, the X-ray dose (the number of X-ray photons) may increase.

Therefore, an X-ray energy level may be adjusted by adjusting the tube voltage, and a strength or a dose of X-rays may be adjusted by adjusting the tube current and the X-ray exposure time. Accordingly, it is possible to adjust an energy level and strength of the radiated X-rays by adjusting the tube voltage or the tube current according to a type or a characteristic of the object (ob).

The X-ray generator 110 uses the X-ray tube 111 to generate X-rays and may radiate the generated X-rays onto the object (ob).

The X-ray detector 120 detects the X-rays that have been radiated from the X-ray generator 110 and transmitted through the object (ob), converts the detected X-rays into an electrical signal, and may obtain X-ray data. In addition, the X-ray detector 120 may provide the obtained X-ray data to the image processing unit 150. In this case, the X-ray data obtained by the X-ray detector 120 may be data on a plurality of frame images, but one or more exemplary embodiments are not limited thereto.

The X-ray detector 120 according to an exemplary embodiment detects X-rays transmitted through the object (ob) by synchronizing with a pulse signal in which X-rays are radiated from the X-ray generator 110 at a predetermined time interval and thus may detect the X-rays that are multiply radiated. In addition, the X-ray detector 120 detects multiply radiated X-rays and may convert the X-rays into X-ray data, which is an electrical signal. Here, the X-ray data may correspond to the plurality of frame images.

In general, the X-ray detector 120 may be classified by a material configuration method, a method of converting detected X-rays into an electrical signal, and a method of obtaining X-ray data. Hereinafter, various methods in which the X-ray detector detects X-rays, the detected X-ray is converted into an electrical signal, and X-ray data is obtained will be described.

First, the X-ray detector 120 is classified as a single element configuration or a mixed element configuration depending on the material configuration method.

When the single element configuration is used, a part in which the X-rays are detected and an electrical signal is generated and a part in which the electrical signal is read and processed are made of a single element semiconductor or are manufactured in a single process. For example, a complementary metal oxide semiconductor (CMOS) or a charge coupled device (CCD) serving as a light receiving element may be used.

When the mixed element configuration is used, a part in which the X-rays are detected and an electrical signal is generated and a part in which the electrical signal is read and processed are made of different elements or are manufactured in different processes. For example, there are a case in which X-rays are detected using a light receiving element such as a photo diode, a CCD, and cadmium zinc telluride (CdZnTe) and an electrical signal is read and processed using a CMOS read out integrated circuit (ROIC), a case in which X-rays are detected using a strip detector and an electrical signal is read and processed using a CMOS ROIC, and a case in which an a-Si or a-Se flat panel system is used.

The X-ray detector 120 may be classified as performing a direct converting method or an indirect converting method according to the method of converting X-rays into an electrical signal.

In the direct converting method, electrons and holes that are temporarily generated inside the light receiving element after the X-rays are radiated move to an anode and a cathode due to an electric field applied to both ends of the light receiving element, and the movement is converted into an electrical signal. In the direct converting method, a-Se, CdZnTe, $HgI_2$, $PbI_2$, or the like may be used as the light receiving element, but one or more exemplary embodiments are not limited thereto.

In the indirect converting method, a scintillator is provided between the light receiving element and the X-ray generator, photons having a wavelength of a visible light range emitted when the X-rays radiated from the X-ray generator react with the scintillator are detected by the light receiving element and converted into an electrical signal. In the indirect converting method, a-Si or the like may be used as the light receiving element, but one or more exemplary embodiments are not limited thereto. In addition, a thin-film gadolinium oxysulfide (GADOX) scintillator, and a micro columnar or needle-shaped CSI (TI) scintillator may be used as the scintillator, but one or more exemplary embodiments are not limited thereto.

A method of obtaining the X-ray data in the X-ray detector 120 may be classified as a charge integration mode in which electric charges are stored for a predetermined time and a signal is obtained therefrom or a photon counting mode in which photons having threshold energy or higher are counted whenever a signal is generated by a single X-ray photon.

The filter 130 is configured to filter the X-rays radiated from the X-ray generator 110 such that a smaller X-ray dose than that in the ROI is incident on the non-ROI. This is used to reduce a total X-ray dose incident on the object (ob).

Specifically, the filter 130 according to the exemplary embodiment allows the X-rays radiated from the X-ray generator 110 to be directly incident on the ROI, which has much useful information about the inside of the object (ob), and allows a dose of X-rays reduced to a certain extent from the X-rays radiated from the X-ray generator 110 to be incident on the non-ROI.

Figure 7A:
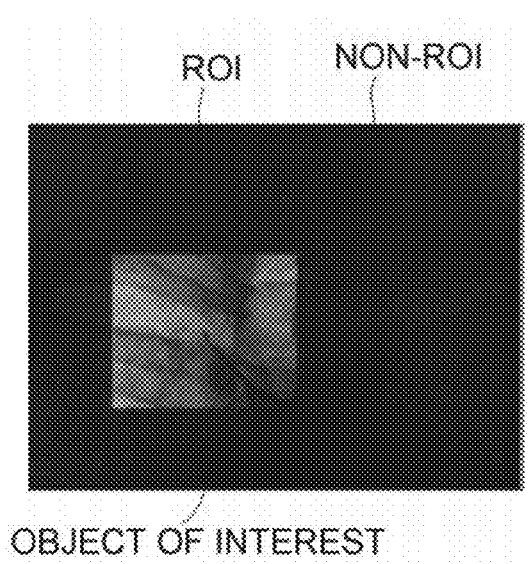
FIG. 7(a) is a diagram illustrating an original X-ray image in which image quality of the non-ROI is degraded significantly more than that of the ROI according to an exemplary embodiment.
Figure 7B:
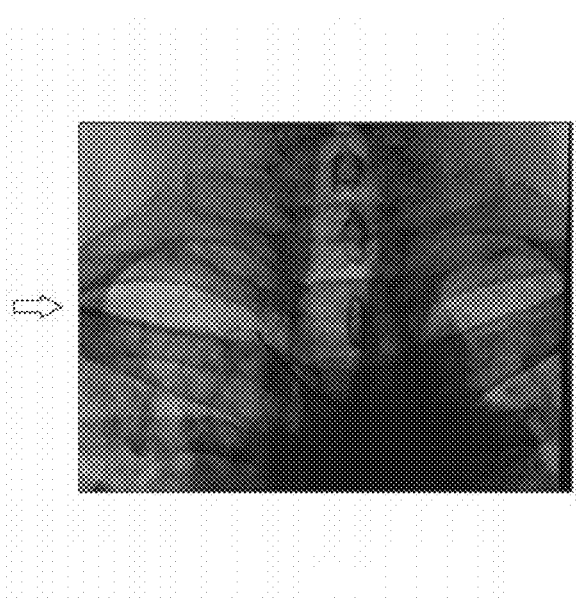
FIG. 7(b) is a diagram illustrating an X-ray image that is reconstructed to register the image quality of the non-ROI to image quality of the ROI according to an exemplary embodiment.

The ROI indicates an area in which an object of interest is positioned. Here, the object of interest refers to an object that is continuously watched by the user while X-ray imaging is performed, and may be understood as an operation site or an instrument used in the object (ob). For example, when the X-ray imaging apparatus 100 is used for angiography, because careful observation on the instrument inserted into a blood vessel such as a guide wire, a catheter, a needle, a balloon, or a stent is desired, this instrument may be set as the object of interest. As illustrated in FIG. 7(a), it can be seen that the object of interest is positioned in the ROI.

In addition, when the operation site is set as the object of interest, a region of stenosis or aneurysm, or a cancerous region may be set as the object of interest.

Figure 4:
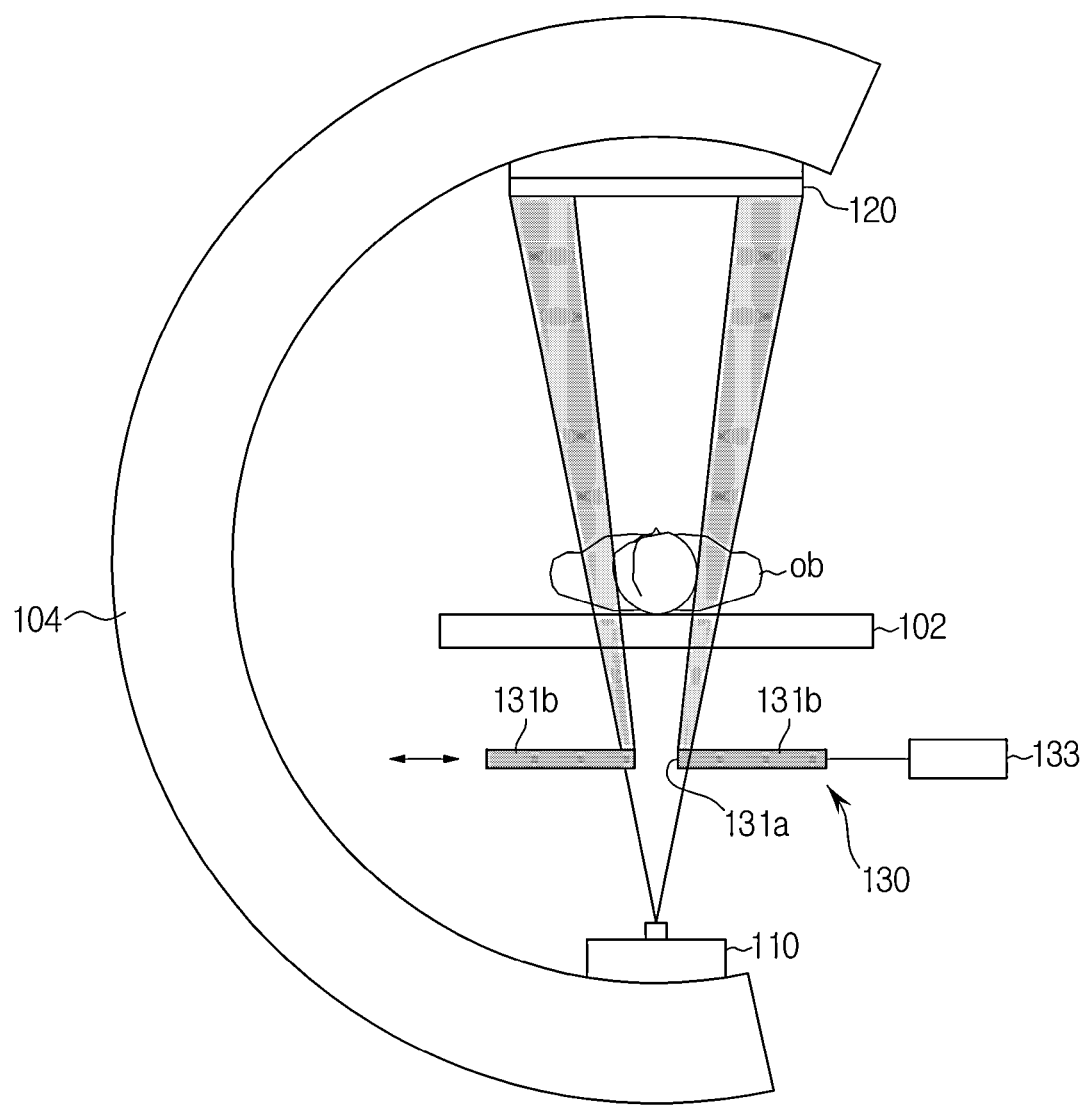
FIG. 4 is a diagram illustrating an X-ray imaging apparatus including a filter according to an exemplary embodiment.

In the exemplary embodiment, as illustrated in FIG. 4, the filter 130 may include a filter 131 and a driver 133 configured to perform translational motion on the filter 131, but one or more exemplary embodiments are not limited thereto.

In this case, as illustrated in FIG. 4, the filter 131 may include an open area 131a and a closed area 131b. Here, the open area 131a may be an area corresponding to the ROI of the object (ob) and the closed area 131b may be an area corresponding to the non-ROI of the object (ob). That is, X-rays transmitted through the open area 131a of the filter 131 may correspond to the X-rays which are radiated from the X-ray generator 110 without change, and X-rays transmitted through the closed area 131b may correspond to X-rays having a dose reduced to a certain extent from X-rays radiated from the X-ray generator 110.

Figure 5:
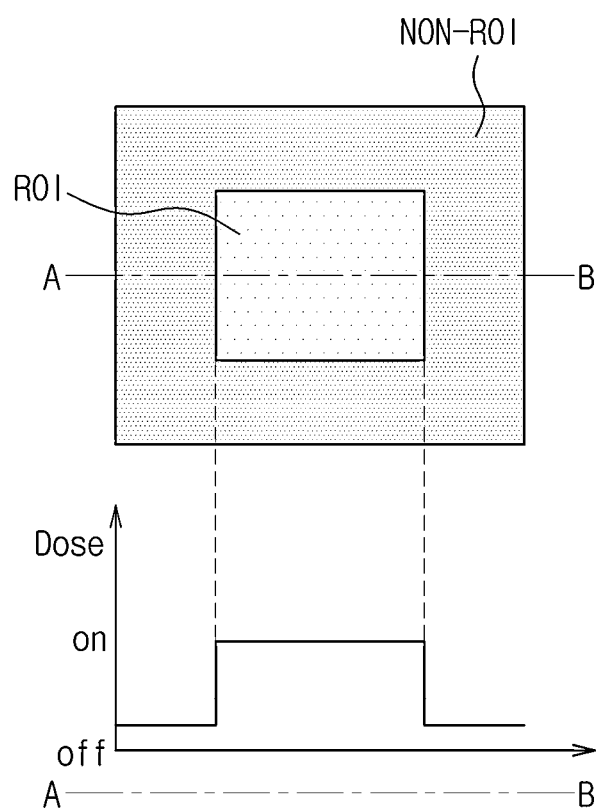
FIG. 5 is a schematic diagram illustrating each X-ray dose incident on a region of interest (ROI) and a non-ROI according to an exemplary embodiment.

When the filter 131 is used, it is possible to adjust the X-ray dose radiated from the X-ray generator 110 according to areas. FIG. 5 is a schematic diagram illustrating a difference between X-ray doses which pass the filter 131 and are incident on the ROI and the non-ROI. That is, as illustrated in FIG. 5, when X-rays incident on an arbitrary straight line AB which crosses the object (ob) having the ROI and the non-ROI are observed, an X-ray dose incident on the non-ROI is smaller than an X-ray dose incident on the ROI.

In this way, because different X-ray doses are incident on the ROI and non-ROI, there is an image quality difference between the ROI and non-ROI in the X-ray image. Specifically, as illustrated in FIG. 7(a), the non-ROI is darker and less clear than the ROI.

Figure 6:
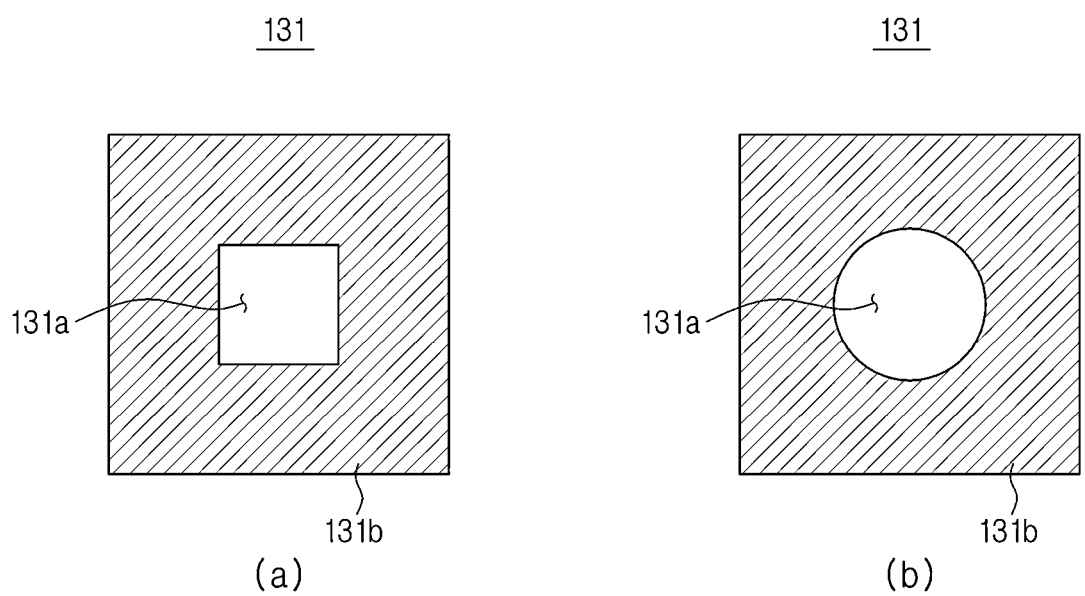
FIG. 6 is a cross-sectional view illustrating an exemplary open area shape of a filter according to an exemplary embodiment.

In the exemplary embodiment, a shape of the open area may be a square as illustrated in FIG. 6(a) or a circle as illustrated in FIG. 6(b). However, these are only examples, and the shape of the open area 131a of the filter 131 is not limited thereto but may be implemented in various other shapes.

As described above, the driver 133 included in the filter 130 is configured to perform translational motion on the filter plane, or filter sheet 131. When the object of interest is an instrument that is inserted into the object (ob) and moves, the ROI also moves as the object of interest moves. Therefore, the driver 133 is used to move the open area 131a of the filter sheet 131 corresponding to the moving ROI according to movement of the object of interest. A motor, a vacuum motor, a pneumatic cylinder, a hydraulic cylinder, or the like may be used as the driver 133, but one or more exemplary embodiments are not limited thereto.

According to another exemplary embodiment, the filter sheet 131 may be an electrically controllable absorptive filter. The driver 130 may provide an electrical current that triggers select portions 131b of the filter to absorb incident X-rays while leaving a select portion 131a such that it does not polarize and absorb incident X-rays. Similar to the above embodiments, the driver 130 may adjust what portions absorb and what portions do not.

According to the exemplary embodiment, the controller 140 (refer to FIG. 2) may generate a control signal and provide the control signal to the driver 133 of the filter 130, and the driver 133 may move the filter 131 according to the control signal received from the controller 140. In this case, various methods may be used as a method of generating a control signal that is provided from the controller 140 to the driver 133 of the filter 130. For example, movement of the instrument serving as the object of interest is tracked in the X-ray image using an object tracking algorithm, tracked trajectory information, that is, movement information, may be used to generate the control signal, but one or more exemplary embodiments are not limited thereto. When the control signal generated using such a method is used, the filter 131 may move in real time in response to the movement of the object of interest. Specifically, it is possible to perform translational motion on the filter 131 so as to move the open area 131a of the filter 131 in response to the movement of the object of interest.

The image processing unit 150 is configured to receive X-ray data from the X-ray detector 120 to generate an X-ray image and generate an X-ray image in which image quality of the non-ROI is reconstructed to register image quality of the ROI in the X-ray image. Specifically, as illustrated in FIG. 2, the image processing unit 150 according to the exemplary embodiment may include an image analyzer 151, an image registration unit 155, and an image synthesizing unit 157, but one or more exemplary embodiments are not limited thereto.

The image analyzer 151 may generate a plurality of frame images based on the X-ray data converted through the X-ray detector 120. In addition, the image analyzer 151 may analyze the X-ray data and set the ROI and the non-ROI. Detailed description thereof will be made as follows.

The image analyzer 151 according to the exemplary embodiment may analyze the X-ray data on the object (ob) and obtain information on the ROI. A method of obtaining information on the ROI in this case will be described below. First, the object of interest is detected from each frame image.

Here, as described above, the object of interest refers to an object that is continuously watched by the user while X-ray imaging is performed, and may be the operation site or the instrument used in the object (ob). In order to detect the object of interest, storing a characteristic of the object of interest may be done in advance, and then detecting an object corresponding to the pre-stored characteristic from each frame image on the object (ob) may be done. The characteristic of the object of interest may include a movement characteristic, an X-ray absorption characteristic, a shape of the object of interest or the like, but one or more exemplary embodiments are not limited thereto.

As described above, the image analyzer 151 according to the exemplary embodiment may detect the object of interest, set an area including the detected object of interest as the ROI, and set an area other than the ROI as the non-ROI. In this case, a position and a size of the ROI may be determined in consideration of a position or a size of the object of interest, or the movement characteristic of the object of interest.

Alternatively, the image analyzer 151 may use information input from the outside to detect the object of interest. For example, when information about a type of the instrument, a type of an operation, an operation site, injection of a contrast medium, or the like is input from the outside, it is possible to detect the object of interest from each frame image based on the input information.

The image analyzer 151 may track the detected object of interest and determine the movement characteristic of the object of interest. Detecting and tracking of the object of interest and obtaining of information on the ROI may be performed in real time according to a frame rate of a plurality of frames input to the image analyzer 151. Here, obtaining of information on the ROI may include detecting and tracking of the object of interest and setting of the ROI based on the result thereof.

The movement characteristic of the object of interest includes information about a position, a movement size, a movement direction of the object of interest, or the like. The movement size may include a speed and movement of the object of interest may have no constant pattern. Therefore, the movement size may include various pieces of information indicating a movement degree in addition to the speed.

The ROI is a constant area including the object of interest and is defined by the object of interest. Therefore, the movement characteristic of the ROI may be determined according to the movement characteristic of the object of interest.

Information on the ROI obtained by the image analyzer 151, that is, the movement characteristic, the position or the size of the ROI, may be transmitted to the controller 140 and used to control the filter 130.

In addition, in addition to information on the ROI, the image analyzer 151 may also obtain information on image characteristics such as noises, brightness, and contrast, which are represented in each of the plurality of frame images. These characteristics may be transmitted to the controller 140 and also used to control X-ray imaging conditions.

The image registration unit 155 according to the exemplary embodiment is configured to register at least one previous frame image to each of the plurality of frame images. Specifically, the image registration unit 155 finds corresponding pixels out of all pixels in at least one previous frame with respect to all pixels in each frame image. In this case, the number of previous frame images that are registered to a single frame image may be set by the user. A final reconstructed frame image is generated by synthesizing the registered previous frame images later. Therefore, it is apparent that the image quality improves as the number of registered previous frame images increases.

When the object (ob) is a living thing (for example, human), a view of imaging the object (ob) is fixed while X-rays are radiated. However, the object (ob) may move within a corresponding view or unintended movement due to respiration or the like may occur. Accordingly, a position of a specific object is continuously changed in each of the plurality of frame images. Therefore, setting a corresponding relation between pixels in each frame image before each frame image is synthesized may be implemented.

In the exemplary embodiment, various well-known methods may be used as a registration method. The registration methods may be classified into two methods. One is a feature-based registration method and the other is an image-based registration method.

Between these two methods, in the feature-based registration method, features of two images to be registered are extracted, common characteristic information of the extracted features is used to set the corresponding relation and the two images are aligned. Examples of features used in this feature-based registration include a feature point, an outline characteristic, an edge, a directional edge, and a gradient. When the feature-based registration is used, it is possible to extract features with less computation and perform registration. However, registration performance may be significantly affected by accuracy of image feature points extracted from two images. In the image-based registration method, a distribution of brightness values of all pixels of an image is used to perform image registration rather than using an individual characteristic of an image. In this method, mutual information and normalized mutual information may be used.

According to the exemplary embodiment, when a human organ is imaged, there may be local motion due to movement or respiration as described above. Therefore, in the exemplary embodiment, a non-rigid registration method capable of correcting local motion of a single pixel in addition to global motion may be used. Here, the global motion refers to motion that can be defined by a single motion parameter and the local motion refers to motion that cannot be defined by a single motion parameter.

The image synthesizing unit 157 is configured to synthesize the plurality of frame images and at least one registered previous frame and generate a plurality of reconstructed frame images.

Figure 8:
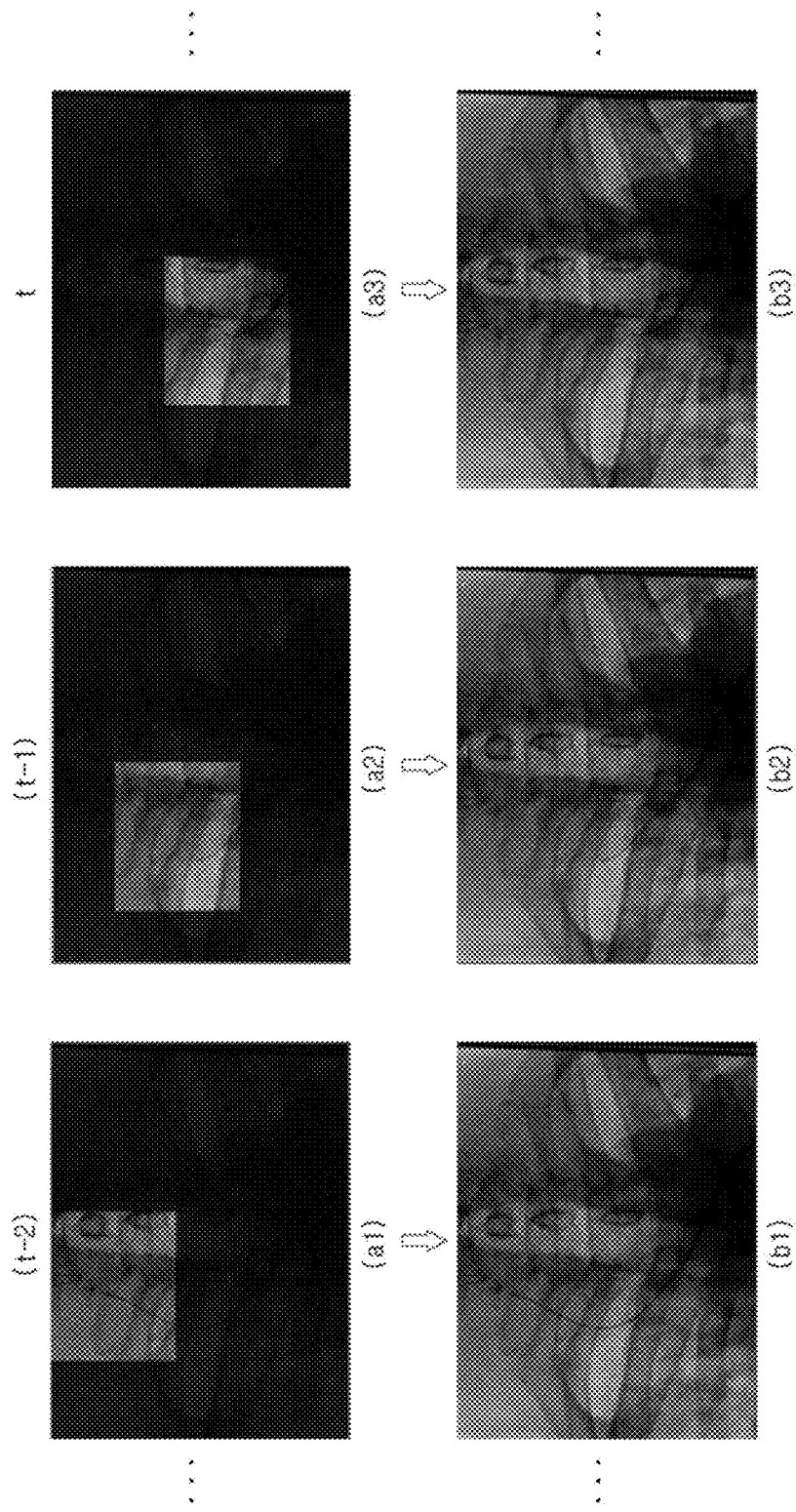
FIG. 8 illustrates an example in which each non-ROI of a plurality of frame images in an X-ray video having a plurality of frame images is individually reconstructed according to an exemplary embodiment.

In the related art, as illustrated in FIG. 8, reconstructed frame images b1, b2, and b3 are generated from a frame image a1 obtained at a previous time point t-2, a frame image a2 obtained at a previous time point t-1, and a frame image a3 obtained at a current time point t using only their own pixel information. That is, only a pixel value of the corresponding frame image a1 is used to determine a pixel value of the reconstructed frame image b1, only a pixel value of the corresponding frame image a2 is used to determine a pixel value of the reconstructed frame image b2, and only a pixel value of the corresponding frame image a3 is used to determine a pixel value of the reconstructed frame image b3. Here, reconstruction using the pixel value refers to removing noises, and adjusting brightness and contrast of each pixel. However, it is difficult to reconstruct the image quality of the non-ROI to the extent of the image quality of the ROI using this method.

Accordingly, in the exemplary embodiment, a method in which a single frame image is synthesized with at least one previous frame and the non-ROI is reconstructed is proposed. For example, when only a value of a pixel A in a current frame is used to determine a value of a pixel A' in a reconstructed frame image of a current frame image, this is the same as the above-described existing method. However, in the exemplary embodiment, in order to determine a value of a pixel A' in a reconstructed frame image of a current frame image, all values of pixels A-1, A-2, . . . , and A-n of previous frames are synthesized with a value of a pixel A in a current frame. As a result, it is possible to generate a robust image in terms of the image quality of the reconstructed non-ROI or noises compared to when the above-described existing method is used. An example of this image synthesizing method will be described in detail below with reference to FIGS. 11 and 12.

In the exemplary embodiment, various well-known image synthesizing methods may be used as the image synthesizing method without limitations. For example, a weighted average method or a method of synthesizing pixel values in the frequency domain may be used, but one or more exemplary embodiments are not limited thereto.

The image processing unit 150 of the X-ray imaging apparatus 100 according to the exemplary embodiment may further include an image adjuster 153. The image adjuster 153 according to the exemplary embodiment may improve the image quality of the non-ROI in the plurality of frame images generated by the image analyzer 151.

As described above, FIG. 7(a) illustrates an X-ray image including the ROI on which an X-ray dose radiated from the X-ray generator 110 is incident without change and the non-ROI on which a smaller X-ray dose than on the ROI is incident due to filtering of the filter 130. As illustrated in FIG. 7(a), the non-ROI on which a smaller X-ray dose than on the ROI is incident has lower image quality than the ROI. For example, it is dark, unclear, and noisy.

Figure 12:
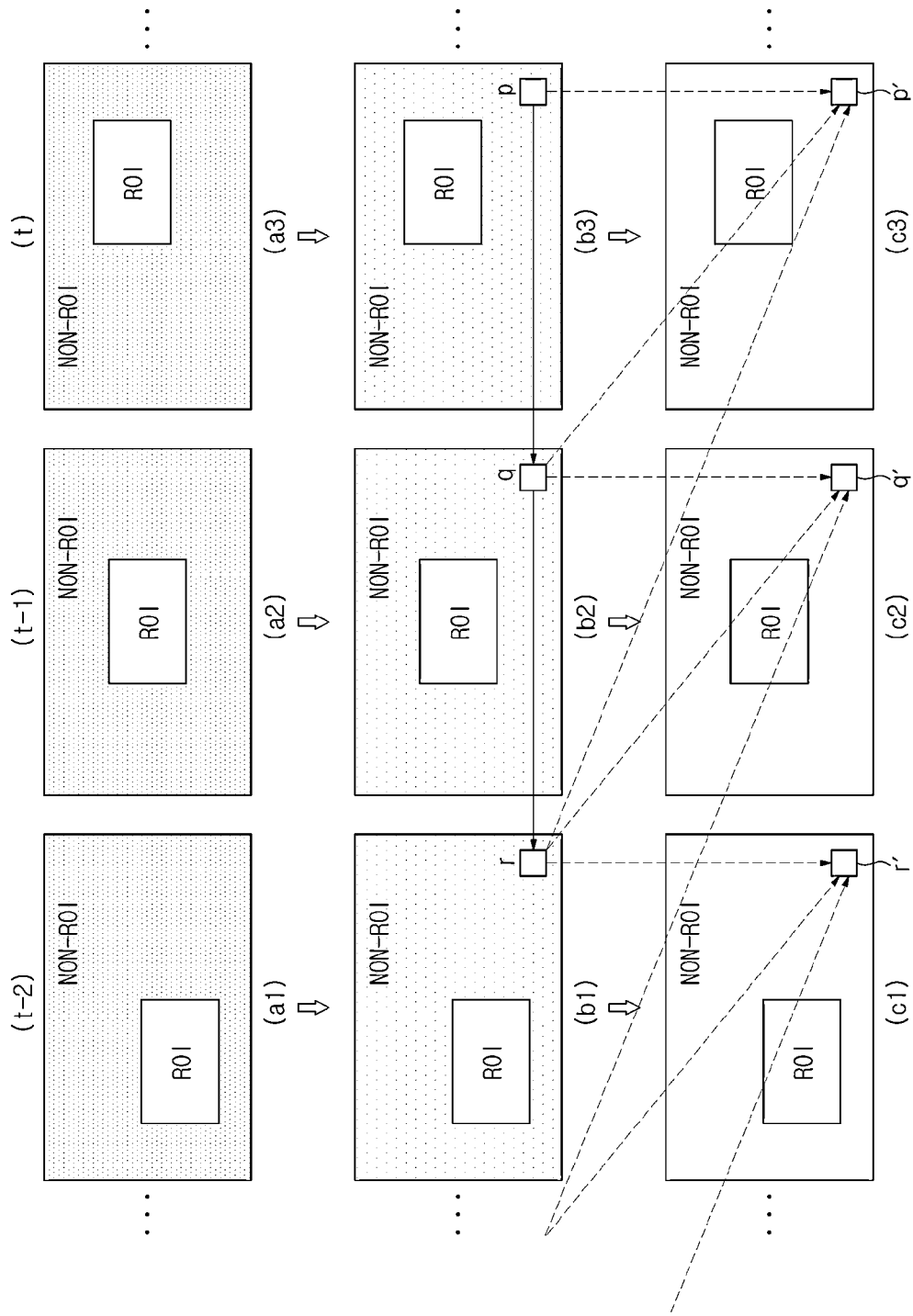
FIG. 12 schematically illustrates of a process of FIG. 10 according to an exemplary embodiment.

In order to reconstruct the non-ROI having low image quality to the extent of the image quality of the ROI through the following frame image registering and synthesizing process, before each frame image is registered, a process of improving the image quality of the non-ROI to a certain extent or higher may provide accurate registration. Therefore, before each frame image is registered, the image adjuster 153 according to the exemplary embodiment may remove noises and adjust brightness and contrast of each non-ROI in the plurality of frame images, and thus improve the image quality of the non-ROI. An exemplary embodiment thereof is illustrated in FIG. 12. Detailed description thereof will be provided when a method is described below.

Figure 11:
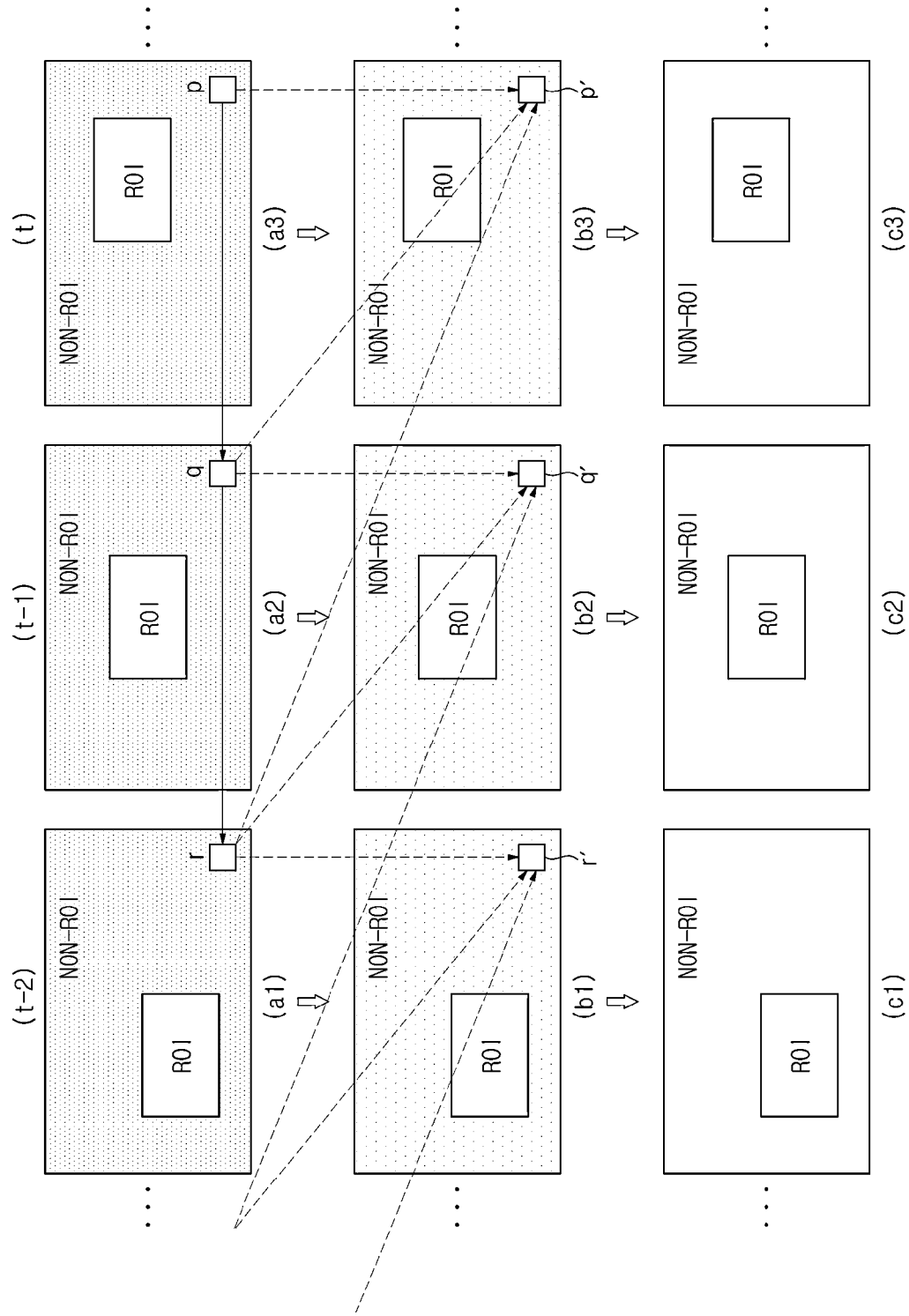
FIG. 11 schematically illustrates a process of FIG. 9 according to an exemplary embodiment.

The image adjuster 153 according to the exemplary embodiment may improve the image quality of the non-ROI in the plurality of reconstructed frame images finally generated by the image synthesizing unit 157. This is an exemplary method of improving the image quality of the non-ROI of the reconstructed frame image finally generated through a registering and synthesizing process rather than improving the image quality of the non-ROI before the frame image is registered as described above. Specifically, the image adjuster 153 may remove noises, and adjust brightness and contrast of the non-ROI of the reconstructed frame image, and thus it is possible to improve the image quality of the non-ROI. An exemplary embodiment thereof is illustrated in FIG. 11. Detailed description thereof will be provided when a method is described below.

The controller 140 may control overall operations of the X-ray imaging apparatus 100.

According to another exemplary embodiment, the controller 140 may include a control signal generator.

When the user inputs a diagnostic command through the input unit 170 connected to the controller 140 via wired and/or wireless communication, the control signal generator may generate a control signal for radiating X-rays and the controller 140 may provide the generated control signal to the X-ray generator 110.

In addition, the control signal generator may generate a control signal for indicating a time interval or frequency at which X-rays are radiated onto the object (ob), that is, a control signal for indicating the time interval and the number of repetitions, together. Similarly, a control signal corresponding to a time interval and the number of repetitions input through the input unit 170 by the user may be generated or a control signal may be automatically generated according to pre-stored data.

The control signal generator may generate a control signal for displaying the reconstructed frame image generated by the image processing unit 150, and the controller 140 may provide the generated control signal to the display 160.

As described above, the control signal generator may generate a control signal for moving the filter 131 in response to the movement of the ROI, and the controller 140 may provide the generated control signal to the driver 133.

The X-ray imaging apparatus 100 according to the exemplary embodiment has been described. The X-ray imaging apparatus 100 according to the exemplary embodiment registers each frame image having the ROI and the non-ROI to at least one previous frame image, synthesizes each frame image and at least one registered previous frame image, and generates a plurality of reconstructed frame images. In this manner, it is possible to obtain an X-ray video having more improved image quality of the non-ROI. Hereinafter, a method of controlling the X-ray imaging apparatus will be described in detail with reference to the accompanying drawings.

Figure 9:
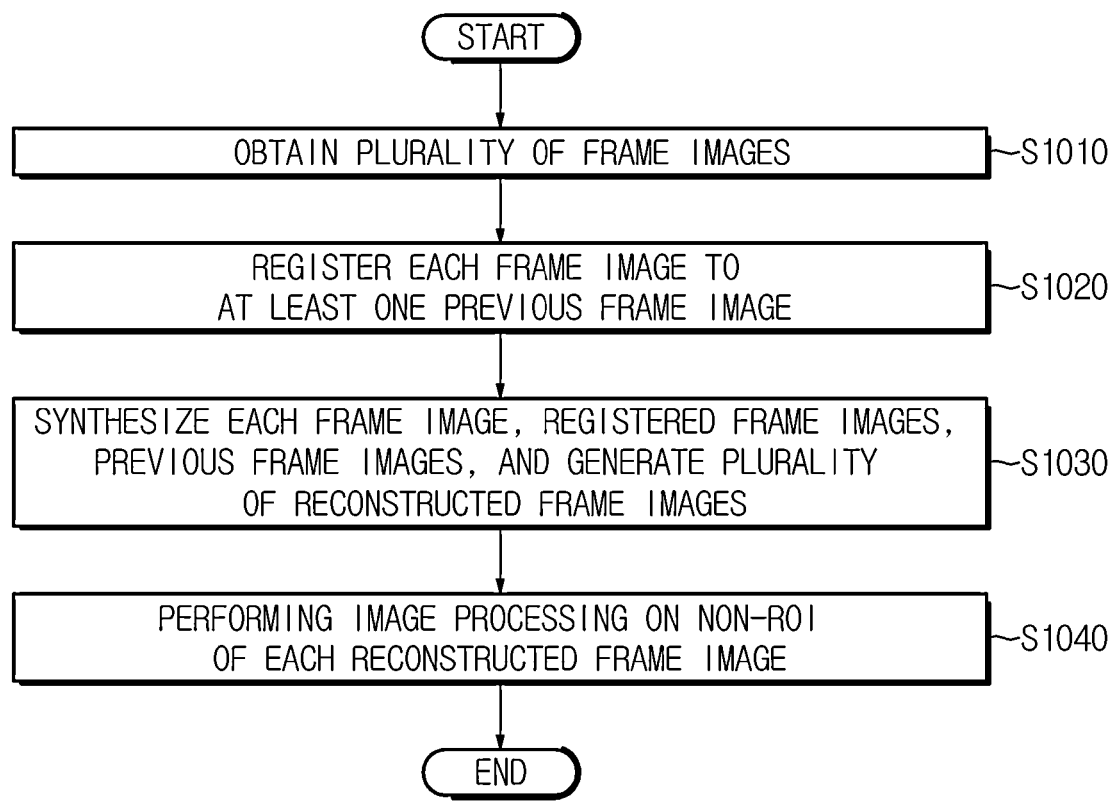
FIG. 9 is a flowchart sequentially illustrating a method of controlling an X-ray imaging apparatus according to an exemplary embodiment.

FIG. 9 is a flowchart sequentially illustrating a method of controlling the X-ray imaging apparatus according to the exemplary embodiment. FIG. 11 schematically illustrates a process of FIG. 9.

The method of controlling the X-ray imaging apparatus according to the exemplary embodiment as illustrated in FIG. 9 will be described below. First, an X-ray video including a plurality of frame images of the object (ob) is obtained (S1010). The video corresponds to a plurality of frame images a1, a2, and a3 illustrated in FIG. 11. In this case, as an exemplary method of obtaining an X-ray video of the object (ob), a method, in which the X-ray generator 110 multiply radiates X-rays onto the object (ob) at a predetermined time interval and the x-ray detector 120 detects X-rays transmitted through the object (ob) at an interval corresponding to the interval of X-rays radiated from the X-ray generator 110, may be used. However, this is only an example and the method of obtaining an X-ray video of the object (ob) is not limited thereto.

As illustrated in FIG. 11, the ROI and the non-ROI may be set in each of the frame images a1, a2, and a3 included in the X-ray video obtained through the operation of S1010. Because the ROI and the non-ROI have already been described, detailed descriptions thereof will not be repeated. In the exemplary embodiment, the X-ray dose incident on the non-ROI may be smaller than the X-ray dose incident on the ROI. This is because, in order to reduce a total X-ray dose incident on the object (ob), X-rays radiated from the X-ray generator 110 are directly incident on the ROI and an X-ray dose reduced by filtering is incident on the non-ROI. As illustrated in FIG. 11, in each of the obtained frame images a1, a2, and a3, the image quality of the non-ROI is remarkably lower than the image quality of the ROI. Therefore, when the display 160 displays the X-ray video, one may reconstruct the image quality of the non-ROI to the extent of the image quality of the ROI.

The exemplary embodiment describes a method of reconstructing the image quality of the non-ROI. According to the exemplary embodiment, in the method of reconstructing the image quality of the non-ROI, each obtained frame image is registered to at least one previous frame image and then each frame image and registered previous frames are synthesized. Hereinafter, a registering operation and a synthesizing operation will be described.

Each obtained frame image is registered to at least one previous frame image (S1020). When the object (ob) is a living thing (for example, human), a view of imaging the object (ob) is fixed while X-rays are radiated. However, the object (ob) may move within a corresponding view or unintended movement due to respiration or the like may occur. Accordingly, a position of a specific object is continuously changed in each of the plurality of frame images. Therefore, one may set a corresponding relation between pixels in each frame image before each frame image is synthesized.

Specifically, corresponding pixels out of all pixels in at least one previous frame with respect to all pixels in each frame image are found. In frame images a1, a2, and a3 in FIG. 11, pixels r, q, and p may be considered to be corresponding pixels. In this case, the number of previous frame images registered to a single frame image may be set by the user. Because a final reconstructed frame image is generated by synthesizing registered previous frame images later, it is apparent that the image quality improves as the number of registered previous frame images increases. Various exemplary embodiments of the image registration method have already been described and detailed descriptions thereof will not be repeated.

Next, each frame image and the registered previous frame image are synthesized and a plurality of reconstructed frame images are generated (S1030). Specifically, pixel information in a current frame image and pixel information in a corresponding previous frame image are synthesized and thus a final reconstructed frame image is generated.

In the related art, as illustrated in FIG. 8, reconstructed frame images b1, b2, and b3 are generated from a frame image a1 obtained at a previous time point t-2, a frame image a2 obtained at a previous time point t-1, and a frame image a3 obtained at a current time point t using only their own pixel information. That is, only a pixel value of the corresponding frame image a1 is used to determine a pixel value of the reconstructed frame image b1, only a pixel value of the corresponding frame image a2 is used to determine a pixel value of the reconstructed frame image b2, and only a pixel value of the corresponding frame image a3 is used to determine a pixel value of the reconstructed frame image b3.

However, in the exemplary embodiment, as illustrated in FIG. 11, a value of a pixel p" of the reconstructed frame image b3 is determined using a value of a pixel p of the corresponding frame image a3, a value of a pixel q of the previous frame image a2, and a value of a pixel r of the previous frame image a1 together. Although the number of previous frame images to be used is two in FIG. 11, this is only an example and the number of previous frame images to be used is not limited thereto. As illustrated in FIG. 11, the reconstructed frame images b1 and b2 are also generated using a pixel value of a corresponding frame image and pixel values of previous frame images.

In the exemplary embodiment, various well-known image synthesizing methods may be used as the image synthesizing method without limitations. For example, a weighted average method or a method of synthesizing pixel values in the frequency domain may be used, but one or more exemplary embodiments are not limited thereto.

Next, image processing is performed on the non-ROI of each reconstructed frame image (S1040). This is an operation of removing noise or the like and adjusting brightness and contrast of the non-ROI when there is an image quality difference between the reconstructed non-ROI and the ROI.

The plurality of frame images obtained through the operation of S1010 are in a state in which uniformity of the ROI and the non-ROI is not corrected and many noises are contained. Therefore, it is difficult to completely improve the image quality when images in this state are synthesized. After the reconstructed frame image is generated, the operation of removing noises or the like and adjusting brightness and contrast of the reconstructed non-ROI is performed, and thus it is possible to further improve the image quality of the non-ROI. FIG. 11 illustrates frame images c1, c2, and c3 which have the improved image quality through performing image processing on each reconstructed frame image b1, b2, and b3.

Figure 10:
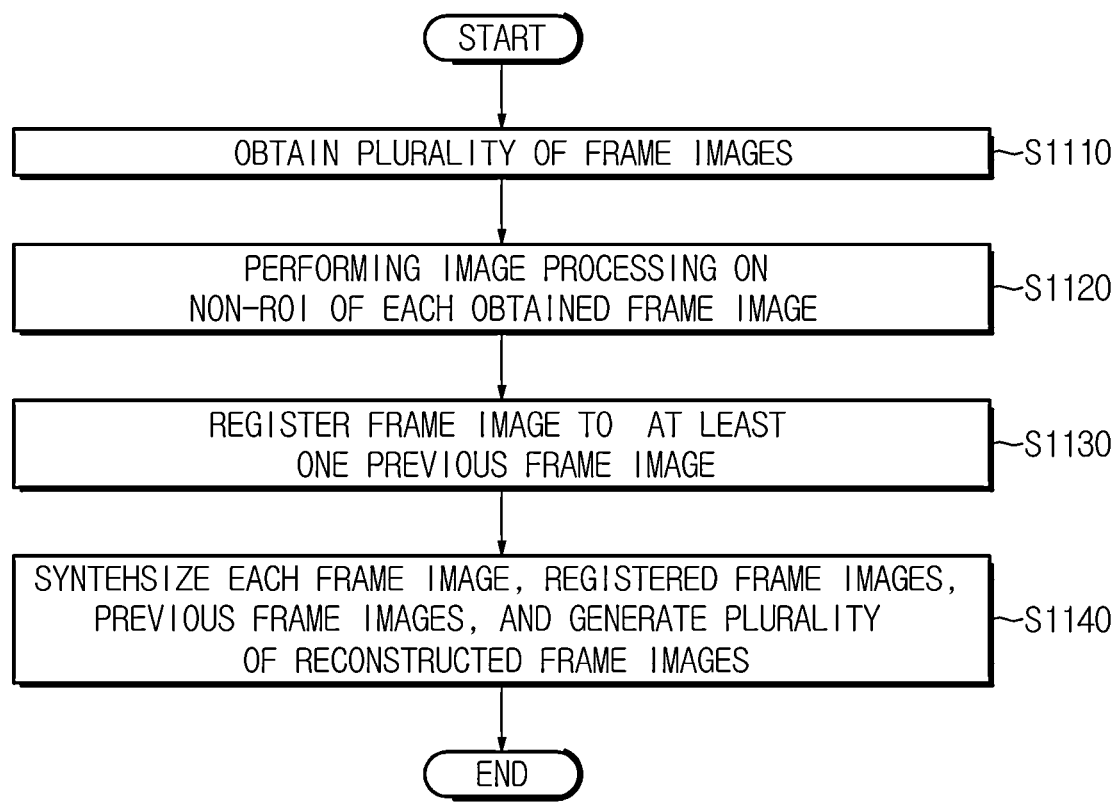
FIG. 10 is a flowchart sequentially illustrating a method of controlling an X-ray imaging apparatus according to another exemplary embodiment.

FIG. 10 is a flowchart sequentially illustrating a method of controlling an X-ray imaging apparatus according to another exemplary embodiment. FIG. 12 schematically illustrates a process of FIG. 10. In this method, because only an order of image processing on the non-ROI is different from the method in the above-described embodiment, this embodiment will be briefly described.

As illustrated in FIG. 10, in the exemplary embodiment, after an X-ray video including a plurality of frame images of the object (ob) is obtained (S1110), image processing is performed on each non-ROI in the plurality of obtained frame images (S1120). That is, as illustrated in FIG. 12, immediately after a plurality of frame images a1, a2, and a3 are obtained, improved frame images b1, b2, and b3 in which brightness and contrast of the non-ROI are adjusted and noises or the like are removed are generated. This allows accurate registration to be performed in the registering operation. Specifically, because the plurality of frame images obtained through the operation of S1110 are in a state in which uniformity of the ROI and the non-ROI is not corrected and many noises are contained, it is difficult to find a corresponding pixel in the registering operation to be performed.

Because image registration performance is dependent on the image quality of the image, when registration is performed using frame images b1, b2 and b3 having the improved image quality rather than using original frame images a1, a2 and a3 having low image quality, it is possible to register more accurately.

Next, in the operation of S1120, each frame image b1, b2, and b3 having the improved image quality is registered to at least one previous frame image (S1130), each frame image b1, b2, and b3 and the registered previous frame image are synthesized, and a plurality of reconstructed frame images c1, c2, and c3 are generated (S1140). In this case, the image registration method and the image synthesizing method have already been described and detailed descriptions thereof will not be repeated.

The exemplary embodiments have been described. In the above-described exemplary embodiments, some components of the X-ray imaging apparatus 100 may be implemented as a kind of module. Here, the term "module" refers to software or a hardware component such as a field programmable gate array (FPGA) or an application specific integrated circuit (ASIC), and the module can perform certain functions. However, the module is not limited to software or hardware. The module may be configured in a recording medium that can be addressed or may be configured to execute at least one processor.

Examples of the module may include software components, object-oriented software components, class components, components such as task components, processes, functions, properties, procedures, subroutines, segments in program codes, drivers, firmware, microcodes, circuits, data, databases, data structures, tables, arrays, and variables. Components and functions provided from modules may be combined into a smaller number of components and modules or may be further separated into additional components and modules. In addition, the components and modules may execute at least one CPU in a device.

Some exemplary embodiments may be implemented through a medium including a computer readable code or instruction for controlling at least one processing component of the above-described exemplary embodiment, for example, a computer readable recording medium. The medium may correspond to a medium or media which enable the computer readable code to be stored and/or transmitted.

The computer readable code may be recorded in the medium or transmitted via the Internet. Examples of the medium may include a ROM, a RAM, a CD-ROM, a magnetic tape, a floppy disk, an optical recording medium, and carrier waves such as data transmission via the Internet. The medium may include non-transitory computer readable media. The media may be distributed over a distributed network and thus the computer readable code may be stored, transmitted, or executed in a distributed manner. Moreover, examples of the processing component may include a processor or a computer processor, and the processing component may be distributed and/or included in a single device.

According to an aspect of one or more exemplary embodiments, it is possible to reduce an X-ray dose incident on the object and obtain a clear X-ray image in which image quality degradation is minimized.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims. Simple modifications and alternations fall within the scope, and the scope is defined by the accompanying claims.

What is claimed is:
1. An X-ray imaging apparatus comprising:
an X-ray generator configured to radiate X-rays onto an object having a region of interest (ROI) determined by a position of an object of interest and a non-ROI, wherein a view of imaging the object is fixed while X-rays are radiated;
a filter configured to adjust an X-ray dose of the X-rays incident on the ROI and the non-ROI;
an X-ray detector configured to detect the X-rays transmitted through the object and convert the X-rays into X-ray data; and
an image processing unit configured to:
analyze X-ray data to obtain a frame image in which the ROI and the non-ROI are set,
register the obtained frame image to a previous frame image, and
synthesize the obtained frame image and the previous frame image to generate a reconstructed frame image,
wherein the filter comprises:
a filter sheet comprising an open area corresponding to the ROI and a closed area corresponding to the non-ROI; and
a driver configured to move the open area of the filter sheet, and
wherein the X-ray imaging apparatus further comprises:
a controller configured to track the object of interest in the obtained frame image, and control the driver of the filter to move the filter sheet such that the open area of the filter corresponds to the ROI determined by the position of the tracked object of interest.

2. The X-ray imaging apparatus according to claim 1, wherein the controller is further configured to provide a control signal to the driver for moving the open area of the filter sheet.

3. The X-ray imaging apparatus according to claim 2, wherein, when the ROI of the object moves, the controller generates the control signal based on movement information of the ROI, provides the generated control signal to the driver, and the driver uses the generated control signal to move the filter sheet such that the open area of the filter sheet corresponds to the moving ROI.

4. The X-ray imaging apparatus according to claim 1, wherein the image processing unit is further configured to adjust brightness and contrast of the non-ROI to have a predetermined value.

5. The X-ray imaging apparatus according to claim 4, wherein the image processing unit removes noise from the non-ROI.

6. A method of controlling an X-ray imaging apparatus, comprising:
radiating X-rays onto an object having a region of interest (ROI) determined by a position of an object of interest and a non-ROI, wherein a view of imaging the object is fixed while X-rays are radiated;
detecting X-rays transmitted through the object;
obtaining a frame image of the object using the detected X-rays;
registering the obtained frame image to a previous frame image; and
generating a reconstructed frame image by synthesizing the obtained frame image and the registered previous frame image,
wherein the radiating X-rays onto an object comprises:
filtering the radiating X-rays such that an X-ray dose on the non-ROI is smaller than on the ROI, and
wherein the filtering the radiating X-rays comprises:
tracking the object of interest in the obtained frame image: and
moving an open area of a filter sheet in the X-ray imaging apparatus such that the open area corresponds to the ROI determined by the position of the tracked object of interest.

7. The method according to claim 6, further comprising:
setting the ROI and the non-ROI in the obtained frame image after the obtaining of the frame image.

8. The method according to claim 7, further comprising:
performing image processing on the non-ROI of the frame image after the setting of the ROI and the non-ROI.

9. The method according to claim 8, wherein the performing of the image processing comprises:
adjusting brightness and contrast of the non-ROI of the frame image to have a predetermined value.

10. The method according to claim 9, wherein the performing of the image processing further comprises:
removing noise from the non-ROI of the frame image.

11. The method according to claim 7, further comprising:
performing image processing on the non-ROI of the generated reconstructed frame image after the generating of the reconstructed frame image.

12. The method according to claim 11, wherein the performing of the image processing comprises:
adjusting brightness and contrast of the non-ROI of the reconstructed frame image to have a predetermined value.

13. The method according to claim 12, wherein the performing of the image processing further comprises:
removing noise from the non-ROI of the reconstructed frame image.

* * * * *